United States Patent [19] [11] 4,221,213

Gregory et al. [45] Sep. 9, 1980

[54] HEADPIECE (HEAT-SUPPORT) HAVING ADJUSTABLE PADS

[76] Inventors: Ralph R. Gregory, 217 W. Second St.; Peter Benesh, 1910 N. Telegraph, both of Monroe, Mich. 48161

[21] Appl. No.: 915,458

[22] Filed: Jun. 14, 1978

[51] Int. Cl.$^3$ .................... A61F 5/00

[52] U.S. Cl. .................... 128/70; 248/118; 297/405; 5/436

[58] Field of Search .................... 128/33, 70, 71, 72, 128/73, 74, 75, 76 R, 133, 134; 5/435, 436, 437, 440, 442, 52; 297/405, 406, 408, 410, 291, 392, 61; 248/118; 269/328; 4/185 HB, 159, 254; 27/13; D6/200

[56] References Cited

U.S. PATENT DOCUMENTS

| | | | |
|---|---|---|---|
| 662,387 | 11/1900 | Baker | 297/391 |
| 671,299 | 4/1901 | Sibley | 297/405 |
| 830,826 | 9/1906 | DeFontes | 297/408 |
| 1,282,580 | 10/1918 | Hosford et al. | 128/71 |
| 1,717,713 | 2/1916 | Gilkerson | 128/72 |
| 2,492,383 | 12/1949 | Jones | 5/437 |
| 2,571,829 | 10/1951 | Buckley | 269/325 |
| 2,719,577 | 8/1955 | Eyman | 297/391 |
| 3,071,412 | 1/1963 | Meade | 297/391 |
| 3,216,767 | 11/1965 | Lutfy | 297/405 |
| 3,552,797 | 7/1968 | D'Houdain | 297/408 |
| 3,828,377 | 8/1974 | Fary | 128/76 R |
| 3,946,452 | 3/1976 | Eary | 297/392 |
| 4,033,339 | 7/1977 | Roberts et al. | 269/328 |

FOREIGN PATENT DOCUMENTS

| | | | |
|---|---|---|---|
| 1371332 | 7/1964 | France | 128/75 |
| 2283648 | 4/1976 | France | 297/391 |
| 398251 | 2/1974 | U.S.S.R. | 269/328 |

*Primary Examiner*—Robert W. Michell
*Assistant Examiner*—Arthur S. Rose
*Attorney, Agent, or Firm*—Harness, Dickey & Pierce

[57] ABSTRACT

A headpiece is provided for the head end of a table on which a patient lies on a side to have the bottom side of the head engage the headpiece. A plurality of pads are adjustable by the headpiece support so that the head is retained in a fixed position while a chiropractor makes a vertible adjustment.

8 Claims, 7 Drawing Figures

HEADPIECE (HEAT-SUPPORT) HAVING ADJUSTABLE PADS

BACKGROUND OF THE INVENTION

Heretofore, a single pad approximately the size of the present headpiece is employed supporting the head when a chiropractic adjustment is made. The commonly used pad is a unitary element which does not adapt to configuration of differently shaped skulls, thereby lacking sufficient skull lockage. The adjustment must be performed with the head in fixed position, utilizing different head fulcra for various adjustments as readily produced by the headpiece support of the present invention.

SUMMARY OF THE INVENTION

The invention pertains to a headpiece which has three adjustable pads on a base which is releasably secured to a vertically adjustable platform at the head end of a table. Two of the pads are alike except for being of the opposite hand with the adjacent edges hinged to opposite edges of a base to permit the pads to swing upwardly so as to engage opposite sides of the head. A third pad has a socket for receiving a ball on which it is tiltable in all directions, permitting adaptation to the patient's mastoid process for greater reinforcement of the skull. The ball has a square bottom portion which is urged vertically with a predetermined force upward from a square aperture in the base when released from a secured position. The ball and bottom square portion is split along the center and is fulcrumed near the bottom of the ball to produce a locking force on the third pad in any of its angularly adjusted positions. A centrally disposed and horizontally positioned link is pivoted between the ends and is engaged by an adjustable eccentric cylindrical element for moving the ends in the opposite direction and for locking the link in adjusted position. The end of the link opposite to the eccentric cylindrical element has an adjustable stud which releases the square end and moves one side portion thereof toward the other when the handle is moved in one direction for moving the ball halves away from each other for engaging and locking the socket and therefore the supported third pad in an angularly adjusted position. The adjustment is made to the third pad after it has been manipulated to provide an engagement in the area of the bottom mastoid to provide a central engagement with the head between the engagements made by the like pair of pads. With the headpiece, the head is readily secured in the position in which it was in when engaged by the three pads so that it cannot shift laterally or rotate when adjustment is made.

BRIEF DESCRIPTION ON THE DRAWINGS

DESCRIPTION OF THE PREFERRED EMBODIMENT

Figure 1:
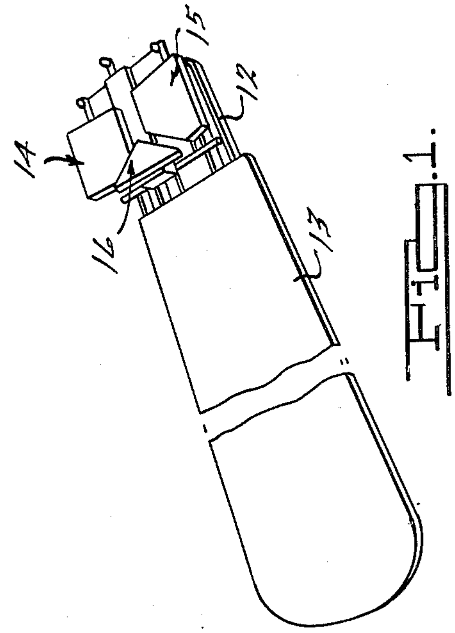
FIG. 1 is a plan view of a table which supports the body of a patient with vertically adjustable headpiece at the head end.
Figure 2:
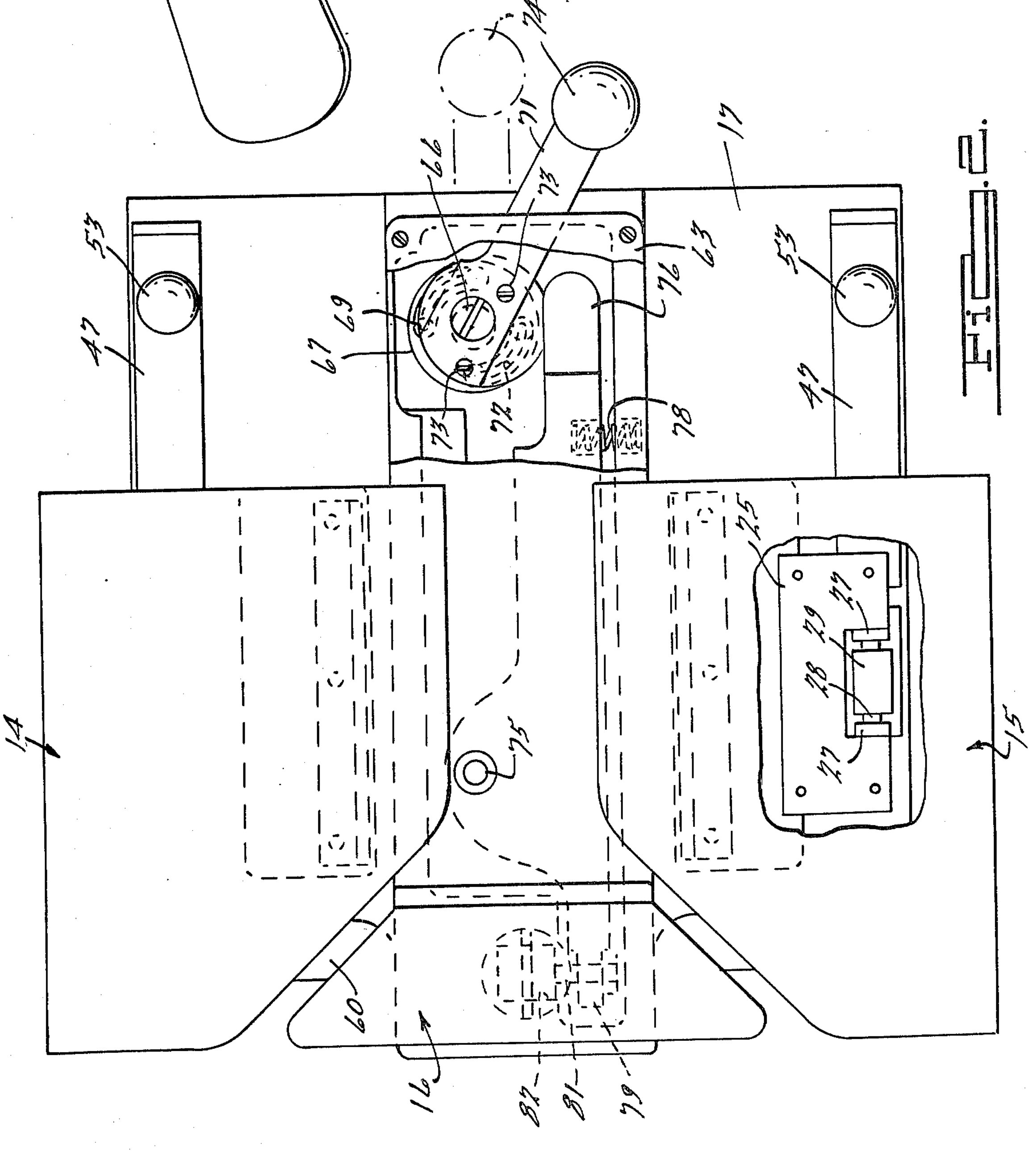
FIG. 2 is a plan view of the headpiece with the right-hand edge disposed adjacent to the body supporting portion of the table.
Figure 4:
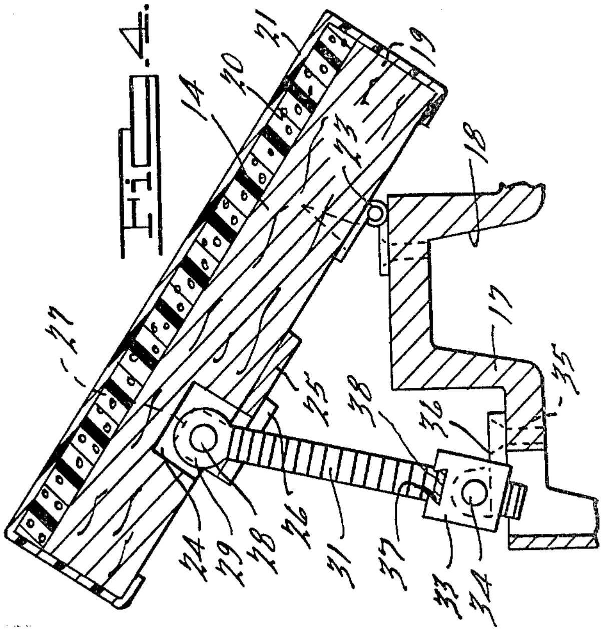
FIG. 4 is a broken sectional view of a hinged pad when in upward tilted position.
Figure 5:
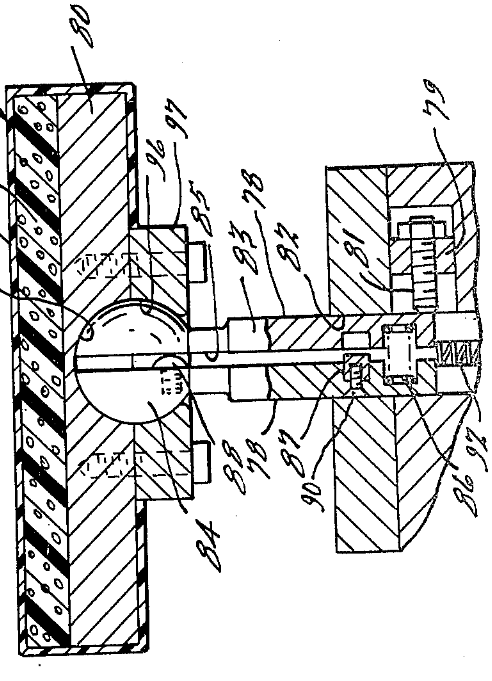
FIG. 5 is a view of the third pad located centrally of the base, with parts broken away.
Figure 6:
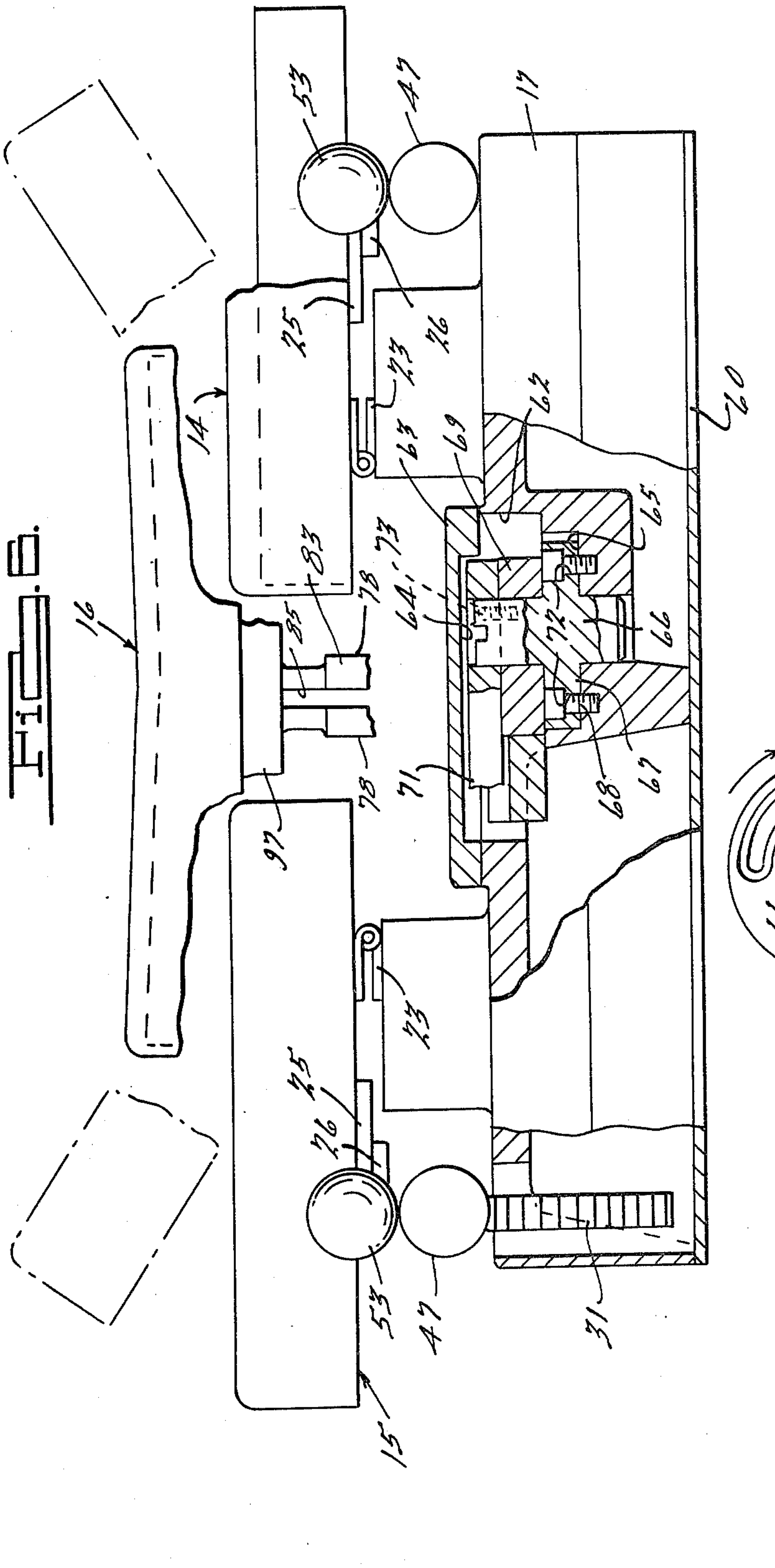
FIG. 6 is a view taken at the right-hand edge of the headpiece illustrated in FIG. 2, with parts broken away.

The headpiece is illustrated in FIG. 1 as being mounted on a platform 12 at the head end of a table 13. The patient lies on the right or left side with the head resting upon the three adjustable pads 14, 15 and 16 mounted for movement upwardly to engage the head and prevent it from moving laterally and rotatably while a chiropractic adjustment is being made. A base 17 is a casting which is cored out at 18 to reduce the weight thereof and provide support for the pads. As illustrated in FIG. 4, the pad 14 and 15 are of like construction except for being of the opposite hand requiring only one to be described in detail. The pad 14 is of rectangular construction except for one corner which is cut off on an approximately 45° angle. The pad 14 is built on a base 19 which is a block of wood having a layer of plastic 20 adherred to the top thereof. The pad may have a sheet of plastic material or may be dipped in a plastic to form a cover 21 which encloses the block 19 and plastic layer 20 and provides a sanitary pad. The underside of the block 19 is secured by a hinge 23 to an upwardly extending boss located inwardly of the side of the base 17. The block of wood, metal, plastic or the like 19 has a recess 24 extending thereinto from the underside in which a U-shaped plate 25 is secured by a plurality of screws. A pair of brackets 26 have extending bosses 27 with a hole therethrough which extends therethrough and supports a semi-cylindrical end 29 of a toothed ratchet 31. The ratchet 31 is of rectangular shape and extends through a rectangular aperture 32 in a pivoted element 33 having trunnions 34 on opposite ends. A pair of the brackets 36 are attached by screws 35 to the base 17. The trunnions 34 are disposed in apertures in the bosses 27 to permit it to rock thereon. This is necessary to permit the tooth ratchet 31 to change its angular position as the pad 14 is hinged upwardly different angular amounts. The pivoted element 33 has a dovetail slot 37 at the top in which a dovetailed latch 38 is slidably supported with a forward end 39 in position to engage the teeth of the ratchet 31 to maintain the pad 14 in different adjusted positions.

Figure 3:
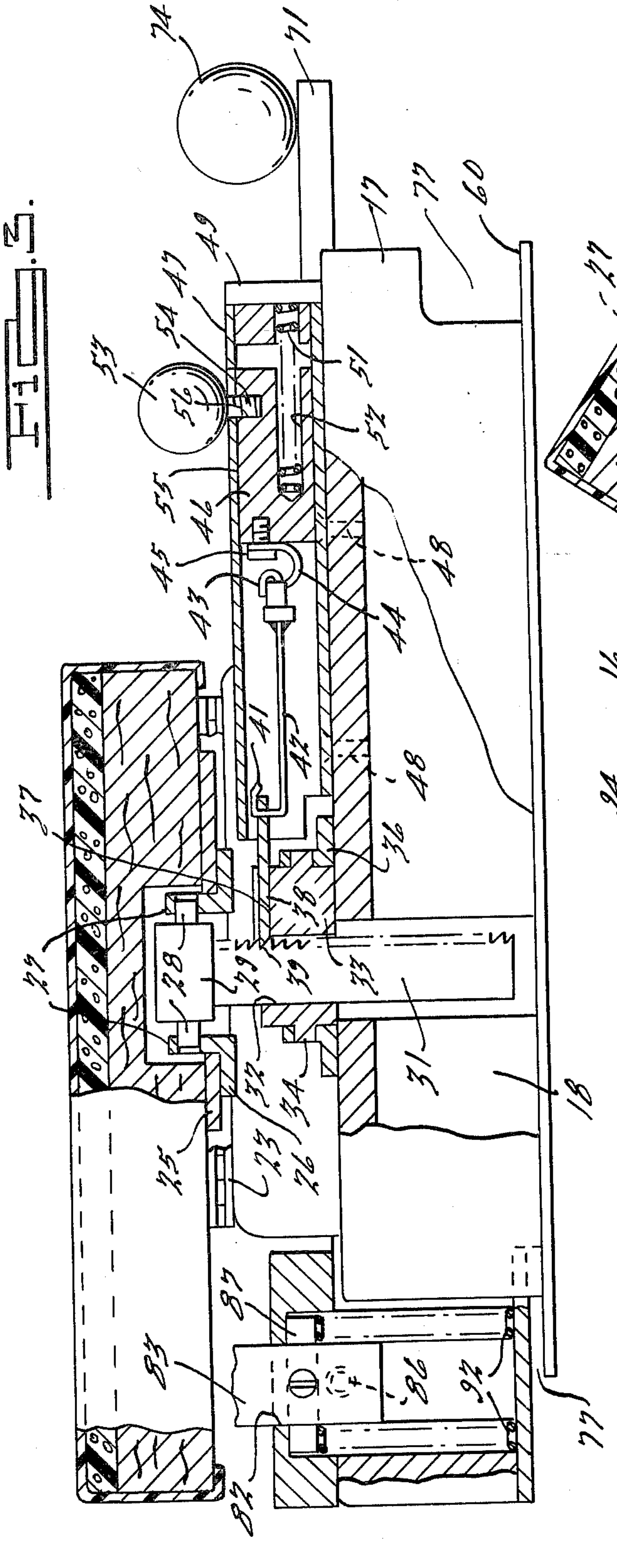
FIG. 3 is a broken sectional view of the structure illustrated in FIG. 2.

As illustrated in FIG. 3, the dovetailed latch 38 has a hook 41 of a wire 42 secured thereto, the opposite end of the wire having a hook 43 which is secured to a U-shaped element 44 attached by a screw 45 to the outer end of a plunger 46 disposed within a tubular element 47. The tubular element 47 is secured by a pair of screws 48 to the base 17. The end 49 of the tubular element 47 has a spring 51 abutted thereagainst, the opposite end extending within an aperture 52 in the plunger 46. This urges the end 39 of the latch 38 against the teeth to have them ratchet thereover until the pad 14 is in adjusted position where it is maintained by the latch.

A ball 53 has a stud 54 extending through a slot 55 in the tubular element 47. The stud is secured in a threaded aperture 56 in the plunger 46 for retracting the plunger and therefore the latch 38 to release the end 39 from the ratchet so that the pad 14 can return to horizontal position. The pad 14 and the supporting adjusting mechanism above described is similarly applied to the pad 15 which is hinged to the base 17 on the righthand side of the headpiece so that when both are adjusted upwardly, an adaptable V-shaped recess is formed which anchors the head in relatively fixed position.

Figure 7:
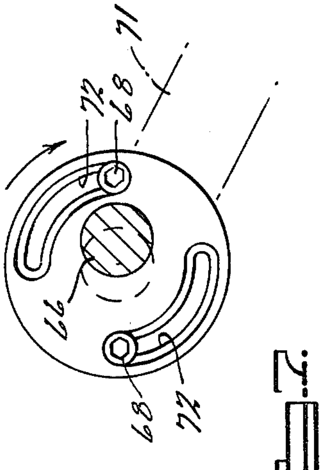
FIG. 7 is a view of the eccentric lock which clamps and releases the support for the third pad at the right-hand edge of the structure illustrated in FIG. 2 and which locks the pad in any angular adjusted position.

A further anchor for the head is provided by the third pad 16 located centrally of the base between the pair of cut-off corners of the pads 14 and 15. A central horizontally extending recess 62 is provided in the base 17 enclosed by a cover 63 which has a recess 64 in the underside of its forward end. A circular recess 65 is provided in the bottom of the recess 62 for receiving a stud 66 having a circular flange 67 which is secured in the recess 65 by a plurality of screws 68. A circular cam element 69 is mounted on the stud 66 for rotation thereabout. A handle 71 is secured to the top of the cam 69 by a pair of screws 73 extending through arcuate slots 72 through the cam element 69, as shown in FIG. 7. A knob 74 is attached to the end of the handle by which it is angularly adjusted. Within the recess 62 is a lever 76 mounted for angular adjustment about the stud 66. The forward end of the lever 76 is urged against the cam 69 by a spring 78, the opposite end 79 of the lever 76 has an adjustable stud 81 extending toward a vertically disposed square aperture 82 in which the square end 83 welded or otherwise secured below a ball 84 is disposed for engagement by the stud 81. The square end 83 and ball 84 are split downwardly through the middle at 85, the rectangular ends being forced away from each other by a spring 86 disposed therebetween. A finger 87 secured by a screw 90 is fixed between the rectangular sections 78 of the square end 83. An arcuate head 88 of a screw is supported by its stud in an aperture in one of the ball halves in position to engage the face of the other ball half to provide a fulcrum therebetween near the bottom of the ball. The head 88 forms a fulcrum which forces the semi-cylindrical portion of the balls apart when the end of the stud 81 is moved toward the adjacent section of the square end 83 to provide a clamp for securing the pad 16 in adjusted position vertically and angularly. The rectangular sections are moved toward each other against the tension of the spring 86 as the semi-cylindrical ball portions are moved away from each other to clamped position. The pad 16 has a metal plate 80 with a plastic layer 93 adherred thereto and dipped in a plastic material to form an outer layer 94. A semi-spherical aperture 96 is formed in the central part of a clamping plate 97 between the two ends to permit the pad 16 to be angularly adjusted on the split ball 84 to a desirable angular position in which it is locked when the two portions 78 of the square end 83 are moved toward each other. Normally, the pad 16 has the square end moved downwardly in the slot 82 which compresses a pair of springs 92 engaged with the bottom of the a split square end 83. Normally, the springs 92 are compressed when the pad 16 is moved downwardly and disposed in the plane of the pads 14 and 15. After the pads 14 and 15 are adjusted in angular relation to each other when the head of a patient rests thereon, the ball 74 of the handle 71 is moved to the left to move the adjacent end of the lever 76 outwardly by the cam element 69 to permit the stud 81 on the opposite end to move away from the square end 83 to permit the springs 92 to move the ball 84 and pad 16 upwardly against the head in the area of the mastoid to apply a pressure thereagainst. When the adjustable stud 81 moves against the spring pressed rectangular end of the ball 84, it locks the ball 84 in vertical position and the pad 16 in angularly adjusted position. By resting the head on the three pads in this manner, it is stabilized as the chiropractor makes an adjustment while the head is maintained in absolutely rigid fixed position against any movement.

A plate 60 is secured to the bottom of the base 17 to extend adjacent the top and bottom edges therof to provide recesses 77 therealong to form slides by which the headpiece is secured to the top of the platform when moved from the left to the right side thereof.

What is claimed is:

1. In a headpiece for use during a chiropractic treatment of a patient in which said headpiece is secured to a platform at the head end of a table on which a patient lies on the right or left side, a pair of like pads of opposite hand mounted in the same basic plane, a base, hinge-means supporting the adjacent edges of the pads on said base for upward swinging movement out of the basic plane to form a V-shaped recess adapted to engage opposite sides of the patient's head, a third supporting pad mounted on said base in said basic plane so that the three head pads are mounted in the same basic plane while in one position; mounting means for said third pad which permits its tilting and vertical movement relative to the basic plane, said mounting means being positioned such that said mounting means permits said third pad to engage the patient's head in the mastoid area thereof, said mounting means for said third supporting pad including a ball and socket unit permitting the third supporting pad to be tilted in all directions; said socket being mounted on said third pad; said ball having an integral elongated bottom portion and both the ball and the bottom portions being longitudinally split to form split ball and bottom portions; a fulcrum member mounted between said split ball portions adjacent the juncture of the ball and bottom portions about which said split ball and bottom portions pivot to secure the ball in the socket; a spring mounted between the split bottom portions to urge said bottom portions apart; said base having a vertical aperture in which the split bottom portions are disposed for vertical movement; and spring means located between the bottom of the vertical aperture and said slit portions for urging the ball and bottom portions outwardly of said base when the bottom portion is engaged and the split portions are moved toward each other; and locking means to effect movement of the bottom portions for securing said third pad in secured position.

2. In a headpiece as recited in claim 1, wherein a lever is disposed on said base, means pivotally mounting said lever on said base intermediate the ends of said lever, and eccentric means engageable with one end of said lever for moving said one end of the lever, means interconnecting the opposite end of said lever with one of said bottom portions for separating said split ball portions against said socket and thereby locking said ball in the socket and also the third supporting pad in secured tilted position.

3. In a headpiece as recited in claim 2 wherein the end of the lever opposite to that engaged by the eccentric means has an adjustable stud mounted thereon which projects into engagement with one of said bottom portions by which the ball is locked within the socket when the lever has been pivoted and secured in locked position.

4. In a headpiece as recited in claim 3, wherein said like pads have pivoted ratchet teeth, and teeth engaging means spring pressed into ratchet engagement with said teeth for retaining the like pads in adjusted position.

5. In a headpiece as recited in claim 4, wherein all three pads can be disposed at different angles relative to each other.

6. In a headpiece as recited in claim 5, wherein said eccentric means is adjustable to different positions for releasing and clamping the ball unit and locking the lever in adjusted position.

7. In a headpiece as recited in claim 6, wherein a plunger in a cylindrical sleeve is spring-pressed forwardly to operate said teeth engaging means which permits the ratchet element to assume different angular positions relative to the two pads when raised to the same or different angular positions.

8. In a headpiece as recited in claim 7, wherein said ratchet element is pivotally secured to the pair of like pads, and said teeth engaging means is mounted in a pivoted element having a rectangular slot in which said ratchet element is guided.

* * * * *